US008744042B2

(12) United States Patent
Ohzu et al.

(10) Patent No.: US 8,744,042 B2
(45) Date of Patent: Jun. 3, 2014

(54) METHOD FOR DETECTING FINE PARTICLES IN FLUID WITH X-RAY

(75) Inventors: Akira Ohzu, Ibaraki (JP); Fumitaka Esaka, Ibaraki (JP); Kenichiro Yasuda, Ibaraki (JP)

(73) Assignee: Japan Atomic Energy Agency, Ibaraki (JP)

( * ) Notice: Subject to any disclaimer, the term of this patent is extended or adjusted under 35 U.S.C. 154(b) by 751 days.

(21) Appl. No.: 12/929,339

(22) Filed: Jan. 14, 2011

(65) Prior Publication Data

US 2011/0170659 A1 Jul. 14, 2011

(30) Foreign Application Priority Data

Jan. 14, 2010 (JP) ................................ 2010/005933

(51) Int. Cl.
*G01N 23/083* (2006.01)
*G01N 23/12* (2006.01)
*G01N 23/223* (2006.01)

(52) U.S. Cl.
USPC ................................ 378/47; 378/46; 378/51

(58) Field of Classification Search
USPC .......................................... 378/46, 47, 51, 52
See application file for complete search history.

(56) References Cited

U.S. PATENT DOCUMENTS

| | | | | |
|---|---|---|---|---|
| 3,529,151 A | * | 9/1970 | Carr-Brion | 250/362 |
| 3,666,943 A | * | 5/1972 | Carr-Brion et al. | 378/44 |
| 3,749,910 A | * | 7/1973 | Carr-Brion et al. | 378/86 |
| 3,925,661 A | * | 12/1975 | Carr-Brion | 378/44 |
| 3,982,126 A | * | 9/1976 | Von Alfthan | 378/47 |
| 4,125,769 A | * | 11/1978 | Marten et al. | 378/47 |
| 4,388,530 A | * | 6/1983 | Lubecki et al. | 378/45 |
| 4,450,576 A | * | 5/1984 | Lubecki et al. | 378/47 |
| 4,916,719 A | * | 4/1990 | Kawatra et al. | 378/47 |
| 5,107,527 A | * | 4/1992 | Sipila et al. | 378/46 |
| 5,559,853 A | * | 9/1996 | Linders et al. | 378/159 |
| 5,598,451 A | * | 1/1997 | Ohno et al. | 378/44 |
| 5,712,891 A | * | 1/1998 | Benony et al. | 378/47 |
| 5,768,340 A | * | 6/1998 | Geittner et al. | 378/159 |

(Continued)

FOREIGN PATENT DOCUMENTS

| | | |
|---|---|---|
| JP | 11-83767 | 3/1999 |
| JP | 2006-29921 | 2/2006 |

OTHER PUBLICATIONS

Ken Carr-Brion, X-Ray Analysers in Process Control (New York: Elsevier, 1989), pp. 18-21, 67-70.*

*Primary Examiner* — Allen C. Ho

(57) ABSTRACT

A detection apparatus for fine particles in a fluid includes: a flow cell which passes the fluid therein; an X-ray source which irradiates a side face of the flow cell with X-rays; an X-ray detector that detects the intensity of transmission X-rays that the X-rays which have been emitted from the X-ray source have been attenuated by due to the fine particles in the fluid; a fluorescent X-ray detector which detects fluorescent X-rays that are emitted by the fine particles in the fluid due to the X-rays which have been emitted from the X-ray source; and a data processing device which discriminates between fine particles and air bubbles in the fluid based on the fluctuation amount from each reference variable of the intensity of the transmission X-rays and the intensity of the fluorescent X-rays, and calculates the number and the particle diameter of the fine particles.

7 Claims, 4 Drawing Sheets

(56) References Cited

U.S. PATENT DOCUMENTS

| | | | |
|---|---|---|---|
| 5,982,847 A * | 11/1999 | Nelson | 378/47 |
| 6,012,325 A * | 1/2000 | Ma | 378/47 |
| 6,335,959 B1 * | 1/2002 | Lynch et al. | 378/45 |
| 6,668,039 B2 * | 12/2003 | Shepard et al. | 378/45 |
| 6,859,517 B2 * | 2/2005 | Wilson et al. | 378/47 |
| 7,254,212 B2 * | 8/2007 | Saitoh et al. | 378/47 |
| 7,519,145 B2 * | 4/2009 | Warner et al. | 378/47 |
| 8,306,188 B2 * | 11/2012 | Klein | 378/98.9 |

* cited by examiner

CROSS SECTION OF TRANSMISSION X-RAY BEAM (1)

(2)

(3)

METHOD FOR DETECTING FINE PARTICLES IN FLUID WITH X-RAY

CROSS REFERENCE TO RELATED APPLICATION

This application claims the benefit of Japanese Application No. 005933/2010, filed Jan. 14, 2010 in the Japanese Patent Office, the disclosure of which is incorporated herein by reference.

BACKGROUND OF THE INVENTION

1. Field of the Invention

The present invention relates to a method for detecting fine particles contained in a fluid, and particularly to a method for detecting fine particles in a fluid with the use of X-rays.

2. Description of the Related Art

Various measurement techniques such as a sample screening method, a sedimentation method, a sedimentation transmission method using optical transmission, a light or laser diffraction/scattering method including dynamic light scattering, a photon correlation spectroscopy, a light-shielding method, an electrical sensing zone method, an image analysis method (microscopic method), a chromatography method, a cascade impactor method and a specific surface area measurement method are known as measurement or count techniques for fine particles in a powder which is an aggregate of fine particles, the diameters of the fine particles and the like. These techniques are used as appropriate according to object items of measurement concerning a state of a powder sample of a measurement object, a type of a particle size such as an average diameter and a statistical diameter, a distribution of particle sizes and a geometry of the particles such as a shape. The light diffraction/scattering method and the light-shielding method continuously measure or count the number of fine particles or a distribution of particle diameters of the fine particles in a gas or a liquid fluid, by charging the gas or the fluid containing the fine particles into a flow cell which is a narrow flow channel.

The scattering method is a method of irradiating the fine particles in the flow channel such as the flow cell with a laser or light, and measuring scattered light coming from the fine particles. The relationship between the intensity of the scattered light originating in light and the particle diameter of the fine particles is known on the basis of the Mie scattering theory to be that generally when the particles are several microns or smaller, the intensity of the scattered light is proportional to the fifth or the sixth power of the particle diameter, and when the particles are several microns or larger, the intensity of the scattered light is approximately proportional to the square of the particle diameter.

The optical transmission method or the light-shielding method is a method of irradiating the fine particles in the flow channel with light or laser light and measuring the intensity of light which decreases by being shielded. The amount of light decreased by being shielded is generally proportional to the cross-sectional area of the particles, and accordingly is approximately proportional to the square of the particle diameter when the fine particles have a spherical shape. The particle diameter is calculated from the relationship between this amount of the light signal and the particle diameter.

In the scattering method, when the particle diameter of the fine particles becomes large, the relationship between the particle size and the intensity of scattered light becomes complicated, and the intensity of scattered light greatly varies according to the particle shape, which accordingly makes it difficult to accurately measure the particle size. In the light-shielding method, when the particle size becomes small, the amount of shielded light becomes small, and the measurement error of the fine particles becomes large. For this reason, regardless of the type of the fluid, when the particle diameter of the fine particles is several tens of microns or less, the scattering method is often used, and when the fine particles have such a comparatively large particle diameter as several tens of microns or larger, the light-shielding method is often used.

The scattering method and the light-shielding method can be easily developed at a low cost, and accordingly are widely used in academic and industrial fields as an optical particle counter with the use of light or laser light. Examples of the utility of the scattering method can include measurement of aerosols in the general atmosphere, measurement of suspended airborne particles in a clean room and measurement of impure particles in pure water. Examples of the utility of the light-shielding method can include measurement of foreign matter particles having comparatively large particle sizes in liquids such as industrial water which mainly contains mud and industrial liquids like general drainage and lubricating oil. A technique is also widely used which measures a particle concentration or a distribution of particle diameters from the intensity of the whole scattered or transmitted light coming from the fluid without measuring individual particles. Furthermore, there is also a technique of measuring the image of the scattered light or transmitted light, and individually measuring the particles through image processing.

In addition, a large number of techniques have been developed which select or accurately measure the fine particles in a liquid with the use of the light-scattering method. A method has also been developed that measures optically-induced fluorescent light emitted from fine particles, which is generated by irradiation with light or a laser, and identifies the composition of the substance of the fine particles, and the substance such as a fluorescent substance, viable particles, bacteria and pollen.

However, the light-scattering method and the light-shielding method which irradiate the fine particles with light or a laser have a problem of measuring air bubbles contained in the fluid as fine particles, when measuring the fine particles contained in a liquid fluid in a flow cell. Air bubbles in a liquid have a refractive index largely different from that of a liquid passing in the flow channel, and accordingly refract the light on the interface between the liquid and the air bubbles, which results in scattering of the light. For this reason, because the scattering method measures the intensity of scattered light, it results in regarding and measuring air bubbles as fine particles. Because air bubbles scatter the light and decrease the amount of light to show the same effect as that of light-shielding, the light-shielding method results in regarding and measuring air bubbles as fine particles, in a similar way to that in the scattering method. For this reason, when fine particles in the liquid are measured with the scattering method and the light-shielding method, there is a fatal problem that the number, the concentration and the distribution of particle diameters of the fine particles cannot be accurately measured and errant measured data is shown. In addition, when more air bubbles exist in the liquid than the concentration of the fine particles, the effect of the light-scattering or the light-shielding of the light due to the air bubbles becomes remarkable, the effect of the light-scattering and the light-shielding due to the fine particles is strongly interfered by the effect of the light-scattering and the light-shielding due to the air bubbles, and as a result the measurement of fine particles is impossible. Accordingly, in order to suppress the formation of air bubbles in the liquid, separate the air bubbles from the fine particles, or identify and measure only the fine particles, techniques have been developed such as a technique of defoaming by heating, cooling and pressurizing the liquid, a technique of separating the air bubbles with ultrasonic waves, electrophoresis or the like, a technique of separating the air bubbles by a structure of a flow channel, and further a technique of identifying air bubbles by fluorescent light, a technique of removing air bubbles by capturing the air bubbles with a laser, and a technique of identifying air bubbles by analysis of the signal of the scattered light. However, it is difficult to completely separate or remove air bubbles even with these techniques of separating the air bubbles or defoaming, and a few fine air bubbles remain in the portion to be irradiated with the light or the laser in the flow channel. In order to discriminate air bubbles from fine particles as much as possible, and actually measure the fine particles in the liquid with high accuracy, it is necessary to use an ultrasonic wave, an electrophoretic force or a centrifugal force, to pressurize the liquid to a high pressure, to heat the liquid to an extremely high temperature or cool to an extremely low temperature, or to use each of these techniques in combination, which causes a great problem in developing the product of a measurement instrument that such an apparatus for separating the air bubbles becomes complicated and upsized, and further that a final cost concerning the measurement also increases.

In addition, when the fine particles in an oil product such as a lubricating oil are measured, there are also problems in that the optical transparency of incident light or laser light in the lubricating oil decreases due to coloring and the like caused by the deterioration of the lubricating oil, a normal irradiation intensity of the laser for the fine particles in the lubricating oil cannot be obtained because of the decay of the light by the lubricating oil, the intensity of the scattered light by the fine particles in the lubricating oil also decays, and accordingly the number and the particle diameter of the fine particles cannot be accurately measured. Furthermore, when the lubricating oil is contaminated with moisture content due to a operating environment and the like, micelles, which are droplets, are formed, in which one liquid substance is associated with the other in a granular form through emulsification (emulsion), and remarkably increases the scattering of light. Then, the light cannot pass through the liquid, and the measurement of fine particles becomes impossible.

Moreover, in the scattering method and the light-shielding method, when the fine particles to be measured are constituted by the same substance, a correlation is obtained between the intensity of the light signal obtained by the light-scattering or light-shielding and the particle size; but when the fine particles are made from different elemental compositions, the correlation cannot be obtained between the intensity of the signal and the particle size, because the fine particles made from different elemental compositions show different refractive indexes, characteristics of scattering the light, absorbing the light and transmitting the light and the like, which are optical characteristics of the fine particles; and the number of the particles and the particle diameter cannot be accurately measured. In the scattering method, when the fine particles are made from a substance which scatters little light or a substance which absorbs light greatly even though the particle diameter is the same, the intensity of the light signal of the scattered light coming from the fine particles becomes extremely small, and the signal is not counted as a signal, which consequently causes a count loss. Furthermore, even if the fine particles are made from the same substance, the scattering characteristics of the light are different between the case in which the surface shape of the fine particles is uneven and is complicated and the case in which the surface is smooth, and accordingly the particle diameter cannot be exactly measured. In the light-shielding method, even if the fine particles have the same particle diameter, when the substance of the fine particles absorbs little light and has a large transmittance for the light, a light-shielding effect due to the fine particles is small, and the fine particles are not counted as particles similarly to the case in the scattering method, which results in causing a count loss.

A method of detecting fluorescent X-rays which are emitted from an element due to irradiation with X-rays is proposed as a technique of identifying and detecting every element of the fine particles in a fluid (Japanese Patent Laid-Open No. 11-83767 and Japanese Patent Laid-Open No. 2006-29921).

Japanese Patent Laid-Open No. 11-83767 describes a concentration-measuring device for detecting a small amount of Fe and Cu which are substances of an object to be detected in a secondary supplied water in a pressurized light water reactor in a nuclear power plant. Japanese Patent Laid-Open No. 11-83767 discloses a method of detecting fluorescent X-rays which are emitted from a substance of an object to be detected, by providing a filter in a flow cell, collecting the substance of the object to be detected with the filter and irradiating the substance with X-rays.

Japanese Patent Laid-Open No. 2006-29921 discloses a flow-cytometer system of slowly passing a solution containing a sample (cell) through a tube, irradiating the sample with monochrome X-rays of high luminance from a monochrome X-ray irradiation system, and detecting fluorescent X-rays which are emitted from each element in the sample.

However, the technologies described in Japanese Patent Laid-Open No. 11-83767 and Japanese Patent Laid-Open No. 2006-29921 are both directed at detecting a specific element, are restricted to detecting the specific spectrum of the fluorescent X-rays, and accordingly cannot detect all fine particles contained in the fluid.

An object of the present invention is to provide a method and an apparatus which solve problems such as a measurement error due to air bubbles in a scattering method and a light-shielding method, a count loss due to a different element and impossible measurement due to emulsification, and can easily and accurately measure the number, the particle size and the like of fine particles in a fluid, at a low cost.

SUMMARY OF THE INVENTION

The method and the apparatus according to the present invention use X-rays for detecting fine particles in a fluid.

When a substance is irradiated with X-rays, the substance absorbs the X-rays, and the intensity of transmission X-rays attenuates compared to the intensity of incident X-rays. The attenuation of the X-rays by the substance is represented by the following formula (1). An attenuation coefficient $\mu$ is determined by a substance, its density and the energy of X-rays (Chapter 1 in "Nuclear Radiation Detection" supervised by Osamu Nishino, translated by Akira Sekiguchi, written by W. J. Price, 17th edition, published by CORONA PUBLISHING CO., LTD. in 1993).

$$I=I_o e^{-\mu d} \qquad (1)$$

($I_o$: intensity of X-rays incident on substance, I: intensity of X-rays having passed through substance, $\mu$: attenuation coefficient (or absorption coefficient), and d: thickness of substance)

Even if the fine particles are constituted by different elements, substances or the like from others, as long as the fine particles have the same attenuation coefficient $\mu$, by measuring the intensity of attenuated X-rays by the fine particles, a problem of count loss can be solved, which becomes a problem in the light-scattering method or the light-shielding method and originates in the difference of optical characteristics among substances of the fine particles.

X-rays are transmitted through air bubbles almost without being decayed at all in comparison with the case of transmitting through fine particles or a liquid. Air bubbles and fine particles can be discriminated from each other by appropriately setting the energy of irradiating X-rays. Furthermore, X-rays are transmitted through a fluid without being affected by a state of the fluid such as a colored state and an emulsified state of the fluid.

Moreover, when the fluid in the flow cell is irradiated with the X-rays, the fluorescent X-rays peculiar to the element constituting the substance are emitted from the fluid and the fine particles having been irradiated with the X-rays. The energy of these fluorescent X-rays is determined by the elements constituting the substance. Accordingly, by measuring the fluorescent X-rays together with the attenuated intensity of X-rays, not only is the presence or absence of fine particles confirmed but also the type and constituent elements of the substance can be specified. When the fine particles in a gas are measured, since the density of the gas is quite small in comparison with liquid or fine particles, fluorescent X-rays which are emitted from the gas are extremely much smaller than fluorescent X-rays which are emitted from the fine particles, and the elements identified from the spectrum of the fluorescent X-rays are considered as those of the fine particles. When fine particles in a liquid are measured, the fluorescent X-rays from the liquid can also be measured.

The present invention has been achieved on the basis of the above described knowledge, and provides a detection apparatus for fine particles in a fluid including a flow cell which flows a fluid therein, an X-ray source which irradiates the side face of the flow cell with X-rays, an X-ray detector that detects the intensity of transmission X-rays, which fluctuates because X-rays which have been emitted from the X-ray source are affected by the fine particles in the fluid, a fluorescent X-ray detector which detects fluorescent X-rays that are emitted by the fine particles in the fluid due to the X-rays which have been emitted from the X-ray source, and a data processing device which discriminates between fine particles and air bubbles in the fluid based on the fluctuation amount from each reference variable of the intensity of the transmission X-rays and the intensity of the fluorescent X-rays, and calculates the number and the particle diameter of the fine particles; and a method for detecting fine particles in a fluid, including passing the fluid in the flow cell, irradiating the fluid with X-rays, detecting each intensity of the transmission X-rays that the X-rays have been attenuated by due to the fine particles and air bubbles in the fluid, discriminating between the fine particles and the air bubbles based on the fluctuation amount from the previously determined reference intensity of the transmission X-rays, calculating the intensity and the particle diameter of the fine particles, simultaneously detecting a spectrum of the fluorescent X-rays which are emitted from the fine particles, and identifying an element constituting the fine particles.

The present invention includes the following aspects.

(1) A method for detecting a fine particle in a fluid, enabling the number and the particle diameter of fine particles passing through a region to be irradiated with X-rays, to be measured by measuring and analyzing an attenuation rate or a decay rate of the X-rays which have irradiated the fluid and are attenuated or decayed due to the absorption of the X-rays by the fine particle contained in the fluid, and the fluorescent X-rays generated from the fluid, the fine particle, an air bubble and the like excited by being irradiated with X-rays, in real time, in an apparatus for counting and analyzing the fine particles contained in a flow channel of a gas or liquid fluid. Here, the decay rate is expressed by a ratio (I/Io) of the intensity of transmission X-rays (I) which have been decreased by the absorption of the fine particle in the case in which the fine particle is contained in the fluid, with reference to the intensity of transmission X-rays (Io) in the case in which the fine particle is not contained in the fluid.

(2) The method for detecting a fine particle according to aspect (1), wherein the method of irradiating the fluid with the X-rays includes continuously irradiating one part of the fluid which continuously flows through the flow channel region of the fluid having a fine and narrow flow cell shape, with stable thin beam-shaped X-rays from the transverse direction of the flow direction of the fluid, and making the one part transmit the X-rays.

(3) The method for detecting a fine particle according to aspect (1), wherein the method of measuring the number and the particle diameter of the fine particles in the fluid according to the attenuation of the X-rays includes: measuring the intensity of the X-rays which have been transmitted through the flow channel of the fluid, thereby measuring pulses that are caused by the attenuation and decay of the intensity of the transmission X-rays due to the fine particle, which are generated by the passage of the fine particles through the fluid that is being irradiated with the X-rays, and thereby counting the number of the fine particles from the number of the pulses; and measuring the particle diameter of the fine particle from the size of the pulse that is caused by the attenuation of the intensity of the X-rays according to the size of the fine particles.

(4) The method for detecting a fine particle according to aspect (3), wherein the method of measuring the number and the particle diameter of the fine particles in the fluid can clearly discriminate between the fine particle and the air bubble in the fluid in the case of a liquid fluid, according to the size of the pulse which is caused by the increase or decay of the intensity of the transmission X-rays, can discriminate between the fine particle and the air bubble in the liquid, and can measure only the fine particle.

(5) The method for detecting a fine particle according to aspect (1), wherein the method of measuring and analyzing the fluorescent X-rays generated from the fluid, the fine particle and the like excited by irradiation with X-rays, in real time, and thereby measuring the number and the particle diameter of the fine particles, can specify the fine particle from a difference of the energy of the fluorescent X-rays and the intensity of the X-rays between the fluid and the fine particle, can count the fine particles by analyzing the fluorescent X-rays peculiar to the constituent element of the fluid and the fine particle, which are generated from a constituent element of the fine particle or the fluid by continuous irradiation with the X-rays against the fluid or the fine particle passing through the flow channel of the fluid, and can measure the particle diameter from the intensity of the fluorescent X-rays of the fine particles.

(6) The method for detecting a fine particle according to aspect (5), enabling the fine particle and the air bubble in the fluid to be clearly discriminated from each other according to the presence or absence of the fluorescent X-rays or the difference of the energy of the fluorescent X-rays, in the case of a liquid fluid, and enabling only the fine particle to be measured.

(7) The method for detecting a fine particle according to aspect (5), which can specify and measure the constituent element of the fluid and the fine particles passing through the flow channel of the fluid, simultaneously with the measurement of the number and the particle diameter of the fine particles according to the attenuation of the intensity of the transmission X-rays in aspect (3), by measuring and analyzing the fluorescent X-rays generated from the fluid and the fine particle in the fluid.

(8) The method for detecting a fine particle according to aspect (1), which can measure and analyze a correlation such as a relationship between the number and the particle diameter of the fine particles in the fluid and the constituent element thereof, a relationship between the specific particle diameter and the constituent element, and a relationship between a distribution of the particle diameters and the constituent element, in real time, by having both of the method of measuring the number and the particle diameter of the fine particles according to the pulse caused by the attenuation of the intensity of the transmission X-rays due to the fine particles in aspect (3) and the method of measuring and analyzing the fluorescent X-rays from a foreign matter fine particle in aspect (6), in the method of irradiating the flow channel of the fluid with X-rays.

According to the present invention fine particles can be detected according to their elements by measuring the intensity of attenuated X-rays and detecting fluorescent X-rays, without depending on optical characteristics of the fine particles. Because of this, the fine particles can be measured accurately without causing problems such as a count loss of the fine particles, a measurement error due to air bubbles in a liquid, and impossible measurement due to emulsification which have been difficult to solve in a scattering method and a light-shielding method.

According to the present invention the fine particles can be measured in a short period of time with higher accuracy than that of conventional methods. The apparatus according to the present invention has a simple structure because of not needing a device for defoaming, removing and separating air bubbles. Furthermore, the apparatus has an enhanced measurement accuracy for fine particles, and accordingly can easily control the fine particles in the liquid and easily conduct the maintenance, which leads to the enhancement of the quality of the liquid. The enhanced quality of the liquid is useful for the control of foreign matter fine particles in the liquid, in wide industrial applications such as foods, medicines, medical treatment, the chemical industry and industrial machines, in which a liquid industrial product is manufactured or inspected, and can be expected to enhance the productivity of the products and the like. The enhancement of the measurement accuracy leads to stricter quality control for lubricating oils, for instance, further shows effects in measuring the lubricating oils and shortening an analysis period of time, and accordingly as a result, is anticipated to lead to the enhancement of availability factor of machines and the like with the use of lubricating oils, and to the enhancement of the productivity of the machines.

PREFERRED EMBODIMENT OF THE INVENTION

Figure 1:
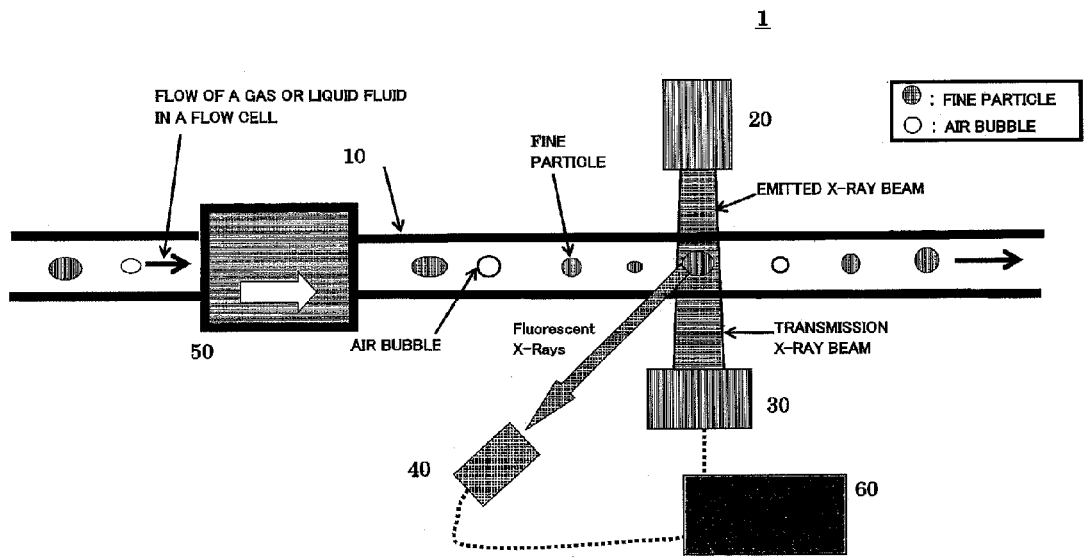
FIG. 1 is a conceptual view of an apparatus for measuring fine particles in a fluid according to the present invention.

The basic conceptual view of the present invention is illustrated in FIG. 1. FIG. 1 schematically illustrates a detection apparatus 1 for fine particles in a fluid, including: a flow cell 10 which passes the fluid therein; an X-ray source 20 which irradiates the side face of the flow cell 10 with X-rays; an X-ray detector 30 that detects the intensity of transmission X-rays that the X-rays which have been emitted from the X-ray source 20 have been attenuated by due to the fine particles in the fluid; a fluorescent X-ray detector 40 which detects fluorescent X-rays that are emitted by the fine particles in the fluid due to the X-rays which have been emitted from the X-ray source; and a data processing device 60 which discriminates between the fine particles and air bubbles in the fluid based on the fluctuation amount from each reference variable of the intensity of the transmission X-rays and the intensity of the fluorescent X-rays, and calculates the number and the particle diameter of the fine particles. FIG. 1 also illustrates air bubbles which are mixed in a liquid when a liquid is used as a fluid.

The flow cell 10 is preferably made from a material which absorbs X-rays little, for instance, a plastic-based material and a thin glass material. In addition, the flow cell 10 is preferably made from a cylinder having a thin wall and a small difference between the outer diameter and the inner diameter of the flow cell so that the transmission intensity of the X-rays does not extremely decrease; and preferably has an inner diameter of such an extent of size as not to be blocked by the fine particles to be measured having a particle diameter, specifically, of a dimension equal to or greater than 1.1 times the maximum particle diameter of the fine particles which are to be measured. Furthermore, in order to prevent the flow cell from being blocked by fine particles having a particle diameter larger than the inner diameter of the flow cell, for instance, when a fine particle having the particle diameter of 400 μm or smaller is measured with a flow cell having the inner diameter of 400 μm, such a filter (not shown) as to prevent a fine particle having the particle diameter of 360 μm or larger from flowing into the flow cell is preferably arranged in the vicinity of the inlet of the flow cell.

The X-ray source 20 is preferably a compact X-ray tube which can stably generate X-rays and is used for normal medical X-ray photography or a non-destructive test, or other X-ray sources which can stably generate X-rays with the use of an electron beam and the like.

The X-ray detector 30 may be a device which can measure the intensity of the X-rays, such as an X-ray photodiode, or may be also a device which can measure an image, such as an X-ray camera. The photodiode can determine the intensity of the transmission X-rays from a signal detected by the photodiode, and the X-ray camera can determine the intensity of the transmission X-rays by integrating signals of each pixel of the image, which shows a signal of the transmission image of the fine particles shown as the image.

The fluorescent X-ray detector 40 is preferably an energy-dispersion type of X-ray energy analyzing device which can detect the intensity of X-rays for each energy of the X-rays with a semiconductor detector or a detector with the use of a scintillator.

In order to pass the fluid into the flow cell, a pump 50 may be arranged by the flow cell 10 or an in-line type of a flow cell may be arranged in a pipe in which the fluid flows.

Next, the method of the present invention will be described below with reference to FIG. 1.

A fluid of a gas or a liquid which contains a group of fine particles is passed into the flow cell 10 that is a fine flow channel, with the use of a pump 50. The fluid that flows in the flow cell 10 and contains the fine particles is irradiated with the X-ray beam in an irradiation region, which has been emitted from the X-ray source 20, continuously irradiates the fluid from the side face of the flow cell 10 in a direction perpendicular to the direction of the flow of the fluid, and has a cross section of a circular or rectangular shape. The X-ray detector 30 detects the intensity of the X-rays which have irradiated the fluid in the irradiation region, have been absorbed by the flow cell, the fluid, the air bubbles and the fine particles, and have passed through them; and the fluorescent X-ray detector 40 detects the excited fluorescent X-rays.

The difference between the intensity of the emitted X-rays and the intensity of the transmission X-rays which is detected by the X-ray detector 30 corresponds to the intensity of the X-rays which have been attenuated by the fluid and the like. Here, the fluid is previously irradiated with the X-rays in such a state that only the fluid is passed in the flow cell, and the intensity of the transmission X-rays is determined and is stored in the arithmetic processing device as the reference intensity of the transmission X-rays. The difference between the intensity of the transmission X-rays which was determined on a test sample and the reference intensity of the transmission X-rays becomes the amount of X-rays absorbed by the fine particles and the air bubbles which are to be measured.

Figure 2:
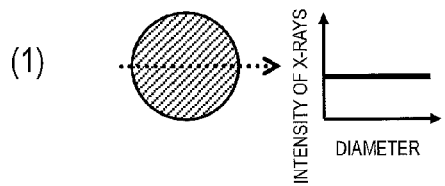
FIG. 2 is an explanatory view illustrating a relationship between a cross section of a transmission X-ray beam and an distribution of the intensity of the transmission X-rays in a diameter direction, in FIG. 1.
Figure 2:
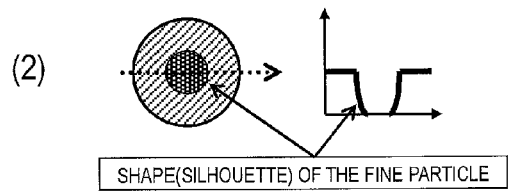
Figure 2:
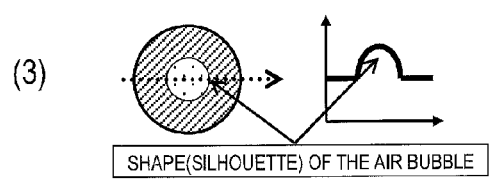

FIG. 2 illustrates a cross section and an X-ray intensity of a transmission X-ray beam. FIG. 2(1) is a case in which there is no fine particle and no air bubble in a region to be irradiated with X-rays (a case of only gas or liquid), FIG. 2(2) is a case in which there are fine particles in a region to be irradiated with X-rays, and FIG. 2(3) is a case in which there is an air bubble in a region to be irradiated with X-rays. As is illustrated in FIG. 2(1), the intensity of the transmission X-rays in the case in which only the fluid was passed in the flow cell is previously determined as the reference intensity of the transmission X-rays. Because the attenuation coefficient of the X-rays, the intensity of the transmission X-rays varies depending on the density of a substance, accordingly if the substances have different densities from each other, the quantities of the transmission X-rays are also different. As is illustrated in FIG. 2(2), for instance, when fine particles are contained in the fluid in the irradiation region, if the fine particles have higher density than that of the gas or the liquid, the attenuation coefficient of the X-rays due to the fine particles is large and the emitted X-rays are absorbed by the fine particles. Accordingly, the intensity of the transmission X-rays in an area corresponding to the shape of the fine particles becomes lower than the reference intensity of the transmission X-rays. In addition, when the fluid in the irradiation region is a liquid containing air bubbles, the amount of the absorbed X-rays by the air bubbles is lower than that by the liquid, and accordingly the intensity of the transmission X-rays in an area corresponding to the shape of the air bubbles becomes higher than the reference intensity of the transmission X-rays, as is illustrated in FIG. 2(3).

In the case of fine particles which are made from a single constitutive substance, or in the case of air bubbles, the intensity of the transmission X-rays decreases or increases depending on the size and the volume of the particles or the air bubbles. The shape portion in the cross section of the transmission X-ray beam shows the cross-sectional area of the fine particles or the air bubbles. When the fine particles or the air bubbles have a spherical shape and a circular cross-sectional area, the decreased intensity or the increased intensity of the transmission X-rays is approximately proportional to the square of the diameter, and accordingly the diameter of the fine particles or the air bubbles can be calculated from the decreased intensity or the increased intensity of the transmission X-rays. Specifically, the particle diameter is determined by previously determining a relationship between the particle diameter and the intensity of the transmission X-rays by using a spherical fine particle of which the particle diameter is already known as a standard, preparing a calibration curve, and comparing the measured value with the calibration curve. When the fine particles are made from various types of constitutive substances, the particle diameter can be shown by an equivalent diameter to that of a standard calibration particle, after having corrected the measured value by using a standard calibration particle in a similar way to that in a correction method for the particle diameter, which is used in a normal optical detector for fine particles.

Figure 3:
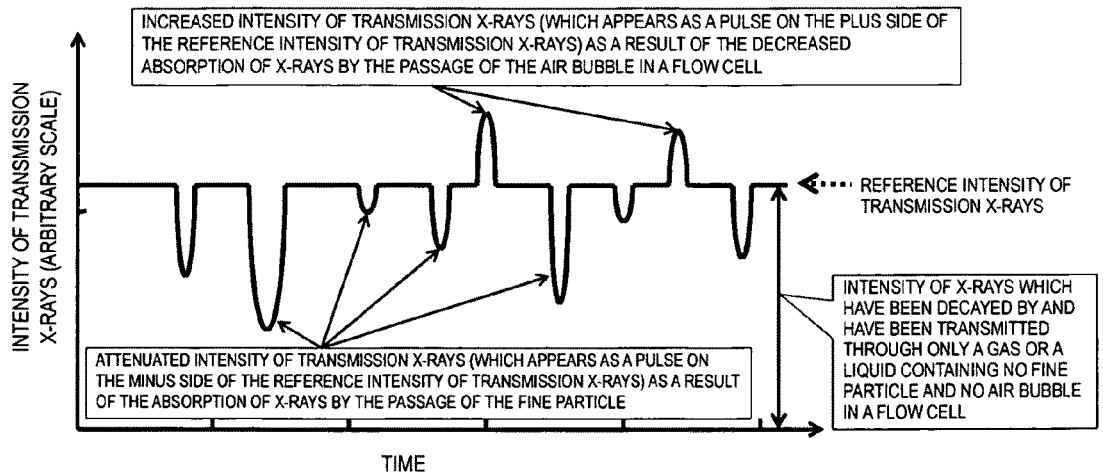
FIG. 3 is a graph showing the change of the intensity of transmission X-rays detected by the apparatus for measuring the fine particles in the fluid in FIG. 1.

When the intensity of transmission X-rays is measured with an X-ray detector when both of fine particles and air bubbles are flowing in a flow cell together with the fluid, a result as shown in FIG. 3 is obtained in principle due to the difference between transmission characteristics of X-rays of the fine particles and the air bubbles in a liquid shown in FIG. 2. When regarding the intensity of transmission X-rays in the case in which there are neither fine particles nor air bubbles in the region to be irradiated with the X-rays in FIG. 2(1) as the reference intensity, a pulse appears in the minus side when a fine particle passes through the region to be irradiated with the X-rays, due to a temporary decay of the intensity of the transmission X-rays, which occurs due to the attenuation of X-rays by the fine particle. In addition, an air bubble absorbs less X-rays than the fluid, and accordingly when an air bubble passes, the pulse appears in the plus side of the reference intensity of the transmission X-rays, in contrast to the case of the passage of a fine particle. Thus, it is possible to discriminate between a fine particle and an air bubble based on whether the pulse signal appears in the plus side or the minus side of the reference intensity of the transmission X-rays. If only pulses which appear in the minus side are measured, only fine particles in the fluid can be detected and the particle diameters can be measured from the number and sizes of the pulses. When the fluid is a gas, air bubbles do not exist and pulses do not appear in the plus side of the reference intensity of the transmission X-rays. Accordingly, the pulses of the fine particles only appear only in the minus side.

Figure 4:
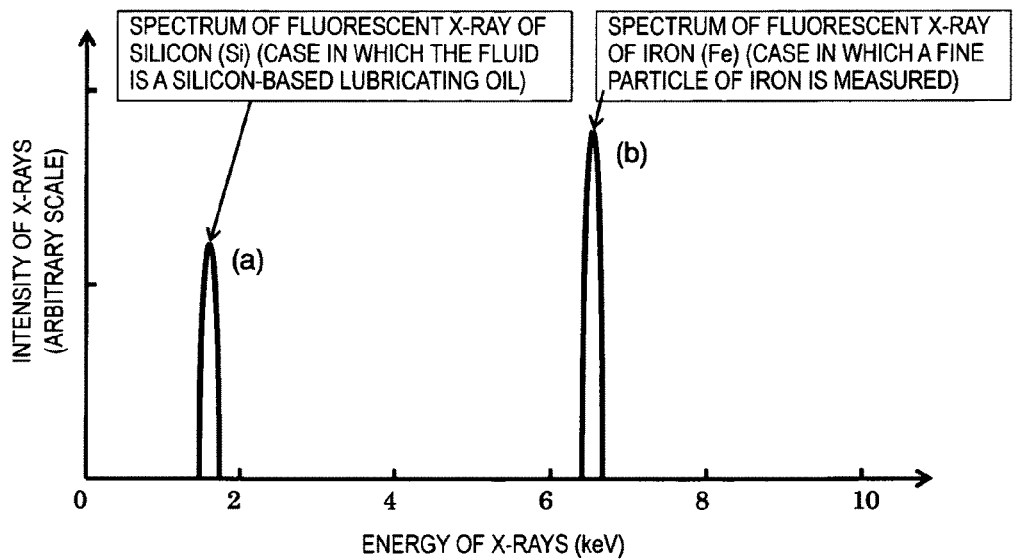
FIG. 4 is a spectrum of the fluorescent X-rays detected by the apparatus for measuring the fine particles in the fluid according to the present invention in FIG. 1, in which (a) shows a peak of Si in a silicon-based lubricating oil, and (b) shows a peak of Fe in the same lubricating oil.

Furthermore, the elements constituting the material of the flow cell and the substance of the fluid and the fine particle are excited by being irradiated with X-rays, and generate fluorescent X-rays peculiar to these elements from the region to be irradiated with the X-rays in the flow cell. By measuring the fluorescent X-rays with a fluorescent X-ray detector 40, a spectrum of the fluorescent X-rays as shown in FIG. 4 is obtained. By measuring the intensity of the transmission X-rays and simultaneously measuring the intensity of the fluorescent X-rays, information concerning the element compositions of the substances of the fine particles is obtained. The information of a spectrum of the fluorescent X-rays emitted from the fluid and the flow cell is preliminarily acquired and is stored as a reference, and then, when a spectrum different from the reference has appeared, the spectrum information at this time becomes the spectrum information of a fine particle or an air bubble. In the case of an air bubble which is formed when the fluid is a liquid, the luminance of the spectrum emitted from the liquid becomes small because the fluorescent X-rays emitted from the fluid decrease. On the other hand, as for a fine particle, it becomes possible to discriminate between a fine particle and an air bubble also from the measurement of the fluorescent X-rays, because the spectra of the fluorescent X-rays peculiar to the elements constituting the fine particle are detected.

As described above, it is possible to detect the elements constituting the fine particles based on the spectrum information of the fluorescent X-rays obtained from the fluorescent X-ray detector 40, by determining the diameter or the content of the fine particles or the air bubbles in the fluid based on the detected value of the intensity of transmission X-rays obtained from the X-ray detector 30.

In addition, it is also possible to detect fine particles only from the detected value of the intensity of the transmission X-rays, when the substance of the fine particles is already known and the information on the spectrum of the fluorescent X-rays is unnecessary as in the case in which the fine particles contained in the fluid are constituted by only one substance.

EXAMPLE

The intensity of transmission X-rays and a spectrum of fluorescent X-rays were detected by using the apparatus of the present invention shown in FIG. 1, and by passing a silicone oil in the flow cell 10, in which powdery fine particles were mixed, which were samples of a residue of a titanium mineral and of which the particle diameters (that were confirmed with an optical microscope) spread in a range of 60 to 150 µm. A glass flow cell was used as the flow cell 10, which had the inner diameter of 0.4 mm, the length of 3 cm and the wall thickness of 0.5 mm. A flow velocity of the fluid in the flow cell 10 was set at 0.1 to 2 cc/min. An X-ray tube was used as an X-ray source 20, and a tube voltage was set at 70 kV.

Figure 5:
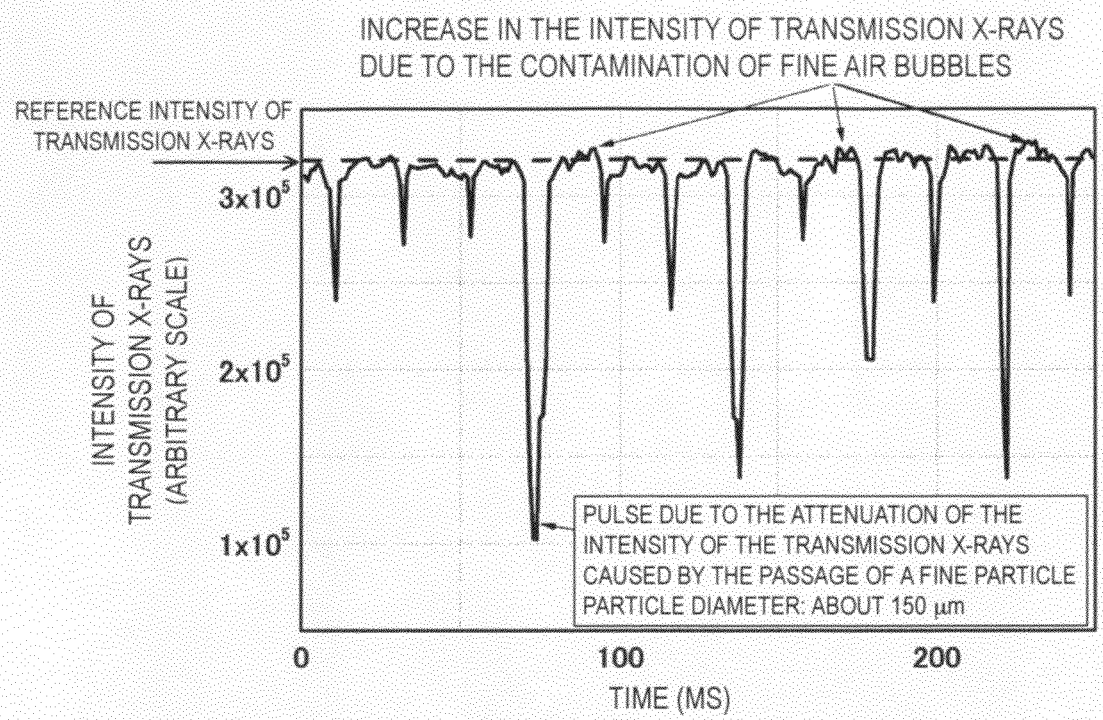
FIG. 5 illustrates signals of the intensity of transmission X-rays in the case in which fine particles in an oil are measured by the apparatus for measuring the fine particles in the fluid according to the present invention, in Example 1.

FIG. 5 illustrates the intensity of transmission X-rays measured while the fluid was passed. A dotted line in the figure shows the reference intensity of transmission X-rays. The point at which the intensity of transmission X-rays exceeds the reference intensity of transmission X-rays appears several times, which suggests that air bubbles exist in the fluid. The peak of the pulse, in which the intensity of transmission X-rays is less than the reference intensity of transmission X-rays, shows the existence of the fine particles in the fluid. It was confirmed that the size (height) of the peak of the pulse, which showed a difference from the reference intensity of the transmission X-rays, had a correlation with the size of the fine particles. If a shape of a particle is assumed to be spherical, the cross-sectional area S is $\pi r^2$ (r: radius of the fine particle), and the cross-sectional area S is proportional to the square of the particle diameter. In addition, if the X-rays are assumed to be almost all absorbed by fine particles, the intensity of X-rays corresponding to the shape area (cross-sectional area S) of the fine particle shown in FIG. 2(2) decreases, and the intensity of the transmission X-rays decays. The amount of the decay (Io−I: size of a peak) is proportional to the size of the cross-sectional area S and proportional to the square of the particle diameter. Specifically, the amount of the decay is expressed by $Io-I \propto S \propto r^2$. When the particle diameter is assumed from the decay peak in FIG. 5 based on this relation, the peak shown in FIG. 5, of which the decay is about 75 ms and largest, corresponds to the largest particle diameter (about 150 µm) that was confirmed with the optical microscope. The amount of the decay of the small peaks at about 55 ms and about 95 ms prior to and subsequent to the largest peak is about one fifth of the largest peak. The ratio of particle diameters corresponds to the one-half power (about 0.45 times) of the intensity ratio of the largest peak, and accordingly the size of the small peaks is about 65 µm. As a result of having observed the used powdery fine particles with an optical microscope, the particle diameter showed a value close to 60 µm, and thereby it was confirmed that the size of the pulse depended on the particle diameter. If a calibration test is conducted by using standard fine particles for calibration, which have different sizes and precisely fixed particle diameters, as in a usual optical fine-particle measurement instrument, the particle diameter can be derived from the size of this peak.

Figure 6:
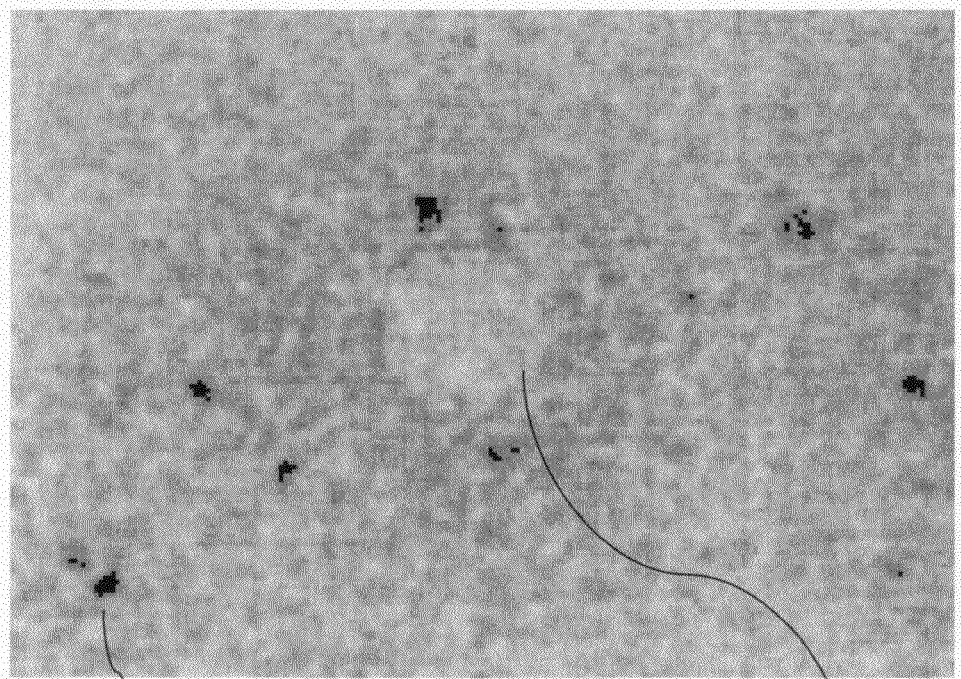
FIG. 6 is an image that shows fine particles in oil, taken with an X-ray camera at the time when the signals of the intensity of the transmission X-rays have been obtained in FIG. 5, which show the presence of air bubbles.

FIG. 6 shows a photograph of the transmission X-rays when the silicone oil which contained powdery fine particles (having the particle diameters of about 60 to 150 µm) that were samples of the residue of the titanium mineral was passed into the flow cell having a rectangular-shaped cross section with a width of 3 mm and a wall thickness of 1 mm. In FIG. 6, a large number of black points show the fine particles, and a circular light-colored portion in the central part shows the air bubble. The reason why a fine particle is shown as a black point is because the intensity of X-rays which have passed through the fine particle decreases compared to the case of only the fluid because of being absorbed by the fine particle, and the reason why an air bubble is shown as a white portion is because the intensity of X-rays which have passed through the air bubble increases compared to the case of only the fluid because an air bubble hardly absorbs the X-rays.

Figure 7:
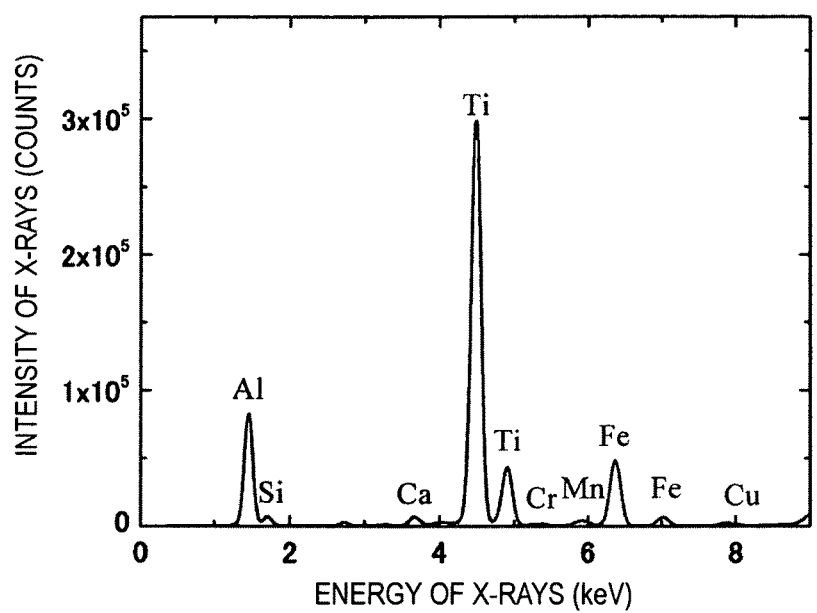
FIG. 7 is a spectrum of the fluorescent X-rays which have been emitted from the fine particles in the oil, in Example 1.

FIG. 7 shows the spectrum of the fluorescent X-rays generated from the fine particles. It is possible to determine the existence of the fine particles from the presence or absence of these spectra and also to find the constituent elements of the substance of the fine particles, by measuring the intensity of transmission X-rays, and at the same time, monitoring the fluorescent X-rays from the flow cell and identifying the spectrum. When there is no fine particle in the region to be irradiated with the X-rays, such a spectrum does not appear, and only the spectrum of the fluorescent X-rays of the material substance of the flow cell and the fluid appears; and when a fine particle passes, the spectrum of the fluorescent X-rays of the fine particle is detected. In the present example, standard powdery fine particles were used which were samples of residue of a titanium mineral containing titanium as a major ingredient and additionally a small amount of impurity elements other than titanium (copper (Cu), calcium (Ca), silicon (Si), iron (Fe) and the like). As shown in the spectrum of the fluorescent X-rays of the fine particles, the spectrum showing the high peak of titanium (Ti) appeared, and accordingly it was confirmed that the fine particles of the sample of the residue of the titanium mineral were included. When an air bubble passed, the spectrum of the fluorescent X-rays from the liquid decreased, and the spectrum of the fluorescent X-rays from the fine particles shown in FIG. 7 did not appear.

In addition, by monitoring this spectrum, it was possible to measure the fine particles containing much titanium while clearly discriminating the fine particles from the air bubbles. Furthermore, if a fine particle formed from another composition passes, this spectrum changes. For instance, if a fine particle containing much iron (Fe) as a major ingredient passes, a spectrum with a high peak of iron is anticipated to appear.

The present invention can be used in the field of the environmental analysis industry that aims at detecting aerosols which float in the atmosphere and contain a specific elements harmful to the human body such as heavy metals, and fine particles which are contained in environmental aqueous solutions such as lake water, river water and ground water, and contain harmful heavy metals; and be used in the field of the nuclear power industry which detects fine particles containing radioactive materials such as uranium and plutonium, and radioactive aerosols, and controls nuclear-related materials. Furthermore, the present invention can be used as means for detecting and analyzing foreign matter particles contained in liquid or gas products in a wide range of industrial fields such as foods, medicines, medical treatment, the chemical industry and industrial machines, in which industrial products such as liquids and gases are manufactured or inspected, and for conducting inspections, maintenance, control and the like of those products and the like.

What is claimed is:

1. A detection apparatus for fine particles in a fluid comprising:
    a flow cell which passes a fluid therein;
    an X-ray source which irradiates a side face of the flow cell with X-rays;
    an X-ray detector that detects an intensity of transmission X-rays that are emitted from the X-ray source and are attenuated due to fine particles in the fluid;
    a fluorescent X-ray detector which detects fluorescent X-rays emitted by the fine particles in the fluid due to the X-rays emitted from the X-ray source; and
    a data processing device which discriminates between the fine particles and air bubbles in the fluid based on a fluctuation amount from a pre-determined reference intensity of the transmission X-rays and an intensity of the fluorescent X-rays, and calculates a number and a particle diameter of the fine particles.

2. The detection apparatus according to claim 1, wherein the X-ray detector can always detect an intensity of the X-rays and is selected from a photodiode, a scintillator X-ray detector or an X-ray camera.

3. A method for detecting fine particles in a fluid comprising:
    passing a fluid in a flow cell;
    irradiating the fluid with X-rays irradiated from an X-ray source;
    detecting with an x-ray detector an intensity of transmission X-rays which fluctuates due to fine particles and air bubbles in the fluid;
    discriminating between the fine particles and the air bubbles with a data processing device based on a fluctuation amount from a pre-determined reference intensity of the transmission X-rays, and calculating a number and a particle diameter of the fine particles with the data processing device; and
    simultaneously detecting with a fluorescent X-ray detector a spectrum of fluorescent X-rays emitted from the fine particles to identify an element constituting the fine particles.

4. The method according to claim 3, wherein if the fluid is a liquid, a detected intensity of the transmission X-rays is counted by the data processing device as a fine particle when the intensity of the transmission X-rays is less than the reference intensity of the transmission X-rays; and is counted by the data processing device as an air bubble when the intensity of the transmission X-rays is more than the reference intensity of the transmission X-rays.

5. The method according to claim 4, wherein calculating a number and a particle diameter of the fine particles comprises:
    calculating, using the data processing device, the number of the fine particles from a number of pulse-shaped signal peaks generated by decreased intensity of transmission X-rays compared to the reference intensity of the transmission X-rays, the pulse-shape of which thus meaning that the intensity of the transmission X-rays is decreased; and
    calculating, using the data processing device, the particle diameter of the fine particles from the peak height.

6. The method according to claim 3, wherein the irradiating is performed with the X-rays continuously irradiating the fluid flowing in the flow cell.

7. The method according to claim 3, further comprising:
    determining, using the data processing device, a calibration curve from a relationship between a particle diameter of a fine particle and the intensity of the transmission X-rays using a control sample; and
    determining, using the data processing device, the particle diameter of the fine particles to be detected by using the calibration curve and a measured value of the intensity of the transmission X-rays.

* * * * *